(12) United States Patent
Godsmark et al.

(10) Patent No.: US 7,989,668 B2
(45) Date of Patent: Aug. 2, 2011

(54) LOWERING NITROGEN-CONTAINING LEWIS BASES IN MOLECULAR SIEVE OLIGOMERISATION

(75) Inventors: John Stephen Godsmark, Grez Doiceau (BE); Georges Marie Karel Mathys, Bierbeek (BE); Hubertus Joseph Beckers, Keerbergen (BE); Charles Morris Yarbrough, Baton Rouge, LA (US); Stephen Harold Brown, Bernardsville, NJ (US); Yeo-Meng Lim, Singapore (SG)

(73) Assignee: Exxonmobil Chemical Patents Inc., Houston, TX (US)

( * ) Notice: Subject to any disclaimer, the term of this patent is extended or adjusted under 35 U.S.C. 154(b) by 1218 days.

(21) Appl. No.: 11/700,979

(22) Filed: Feb. 1, 2007

(65) Prior Publication Data

US 2007/0213575 A1 Sep. 13, 2007

Related U.S. Application Data

(60) Provisional application No. 60/781,623, filed on Mar. 10, 2006.

(51) Int. Cl.
*C07C 2/12* (2006.01)

(52) U.S. Cl. ........ 585/518; 585/500; 585/502; 585/519; 585/520; 585/530; 585/532; 585/533; 585/800; 585/820; 585/823; 585/833; 585/868

(58) Field of Classification Search .................. 585/518, 585/519, 502, 520, 530, 833, 868, 500, 532, 585/533, 820, 823; 208/298; 210/634, 639
See application file for complete search history.

(56) References Cited

U.S. PATENT DOCUMENTS

| | | | | |
|---|---|---|---|---|
| 4,153,638 A | | 5/1979 | Bercik et al. ............. | 585/526 |
| 4,307,254 A | * | 12/1981 | Smith, Jr. ................ | 568/697 |
| 4,973,790 A | * | 11/1990 | Beech et al. ............. | 585/533 |
| 5,414,183 A | * | 5/1995 | Abrevaya et al. .......... | 585/671 |
| 5,446,231 A | * | 8/1995 | Arganbright et al. ....... | 585/802 |
| 5,569,790 A | * | 10/1996 | Frey et al. ............... | 568/699 |
| 5,847,230 A | * | 12/1998 | Cottrell et al. ............ | 568/699 |
| 6,019,887 A | * | 2/2000 | Ramirez de Agudelo et al. ................. | 208/254 R |
| 6,107,535 A | * | 8/2000 | Rossini et al. ............ | 585/823 |
| 6,118,037 A | * | 9/2000 | Piccoli et al. ............. | 585/820 |
| 6,875,901 B2 | * | 4/2005 | Gartside et al. ........... | 585/670 |
| 2002/0103406 A1 | | 8/2002 | Mathys et al. ............ | 585/329 |
| 2004/0097773 A1 | | 5/2004 | Beckmann et al. ........ | 585/530 |
| 2005/0107649 A1 | * | 5/2005 | Cheung et al. ............ | 585/16 |
| 2005/0137442 A1 | * | 6/2005 | Gajda et al. .............. | 585/823 |
| 2005/0152819 A1 | | 7/2005 | Schmidt et al. ........... | 422/190 |

OTHER PUBLICATIONS

Cadogan, et al., "Plasticizers" in Kirk-Othmer Encyclopedia of Chemical Technology, John Wiley, 2000, available on-line Dec. 4, 2000.*

Bahrmann, et. al., "Oxo Synthesis" in Ullmann's Encyclopedia of Chemical Technology, Wiley-VCH, 2005, posted on-line Jun. 15, 2000.*

Stepanov et al., entitled "Interaction of Acetonitrile with Olefins and Alcohols in Zeolite H-ZSM-5: In Situ Solid-State NMR Characterization of the Reaction Products", Chem. Eur. J. 1997, 3, No. 1, pp. 47-56.

* cited by examiner

*Primary Examiner* — In Suk Bullock
*Assistant Examiner* — Bradley Etherton
(74) *Attorney, Agent, or Firm* — Andrew B. Griffis; Leandro Arechederra, III

(57) ABSTRACT

Nitrogen-containing Lewis bases act as poisons for molecular sieve catalysts used in oligomerisation reactions. A lowering of their presence in the feed prior to the contacting thereof with the molecular sieve brings a significant extension of catalyst life. Excessive elimination of these poisons may be disadvantageous. Lowering the levels of these catalyst poisons to more manageable concentrations is therefore preferred.

30 Claims, No Drawings

LOWERING NITROGEN-CONTAINING LEWIS BASES IN MOLECULAR SIEVE OLIGOMERISATION

CROSS REFERENCE TO RELATED APPLICATION

This application claims the benefit of Provisional Application No. 60/781,623 filed Mar. 10, 2006, the disclosure of which is incorporated by reference.

FIELD OF THE INVENTION

The present invention relates to improvements in or relating to oligomerisation reactions that are catalysed by molecular sieves, in particular with zeolites, and which are affected by certain nitrogen containing components brought in by their feedstocks.

BACKGROUND

The condensation reaction of an olefin or a mixture of olefins over a molecular sieve, or in particular a zeolite catalyst, to form higher molecular weight products is widely known. This type of condensation reaction is referred to herein as an oligomerisation reaction, and the products are low molecular weight oligomers which are formed by the condensation of up to 12, typically 2, 3 or 4, but up to 5, 6, 7, or even 8 olefin molecules with each other. As used herein, the term 'oligomerisation' is used to refer to a process for the formation of oligomers and/or polymers. Low molecular weight olefins (such as ethylene, propene, 2-methylpropene, 1-butene and 2-butenes, pentenes and hexenes) can be converted by oligomerisation over a molecular sieve catalyst, to a product which is comprised of oligomers and which is of value as a high-octane gasoline blending stock, which may be used or blended into a distillate type liquid fuel or as a lubricant, or as a starting material for the production of chemical intermediates and end-products. Such chemical intermediates and end-products include high purity hydrocarbon fluids or solvents, alcohols, detergents and esters such as plasticiser esters and synthetic lubricants.

Industrial oligomerisation reactions employing molecular sieve catalysts are generally performed in a plurality of tubular or chamber reactors, similar to those processes employing solid phosphoric acid (SPA) catalysts. With SPA catalysts, the pressure drop over the catalyst bed or beds is increasing gradually over the duration of the run, due to coking and/or swelling of the catalyst pellets, and the reactor run is typically terminated when a maximum allowable pressure drop over the reactor is reached. Molecular sieve catalysts do not show pressure drop increases similar to SPA catalysts. Oligomerisation reactors using molecular sieve catalysts are therefore characterised by longer reactor run lengths, and are typically decommissioned when the catalyst activity has dropped to an unacceptably low level. With these catalysts, the reactor run length that can be achieved is therefore much more sensitive to compounds or impurities in the feed that deactivate the catalyst, such as catalyst poisons. Strong bases, such as the proton bases or Bronsted bases, are known poisons for the molecular sieve oligomerisation catalysts, which are acidic. Such bases in hydrocarbon streams are often nitrogen containing compounds, such as amines and amides, and they are typically removed from feedstocks for oligomerisation reactions, including those using molecular sieve catalysts. Such organic nitrogen-containing Bronsted bases are characterised by at least one hydrogen atom bound to the nitrogen atom, and are known proton acceptors. Other organic nitrogen components do not have any hydrogen atom bound to the nitrogen, and its nitrogen atom may have three bonds to 1, 2 or 3 surrounding carbon atoms. These nitrogen atoms however still have a free electron pair, and therefore can still act as a base, termed a Lewis base. Lewis bases are known to be much weaker bases as compared to Bronsted bases, and therefore are often ignored or not considered poisons to acid catalysed processes.

U.S. Pat. No. 4,973,790 discloses a process for oligomerisation of $C_2$ to $C_{10}$ olefins over a zeolite catalyst comprising a feed pre-treatment step to remove basic nitrogen compounds. It limits itself to the removal of amines such as di-ethanolamine, which are Bronsted bases and have the stronger basicity. It is not concerned with the nitrogen-containing Lewis bases.

U.S. Pat. No. 4,153,638 discloses a process for polymerising $C_2$-$C_5$ olefins to form gasoline and distillate boiling range oligomer products in the presence of a metal-substituted synthetic mica montmorillonite catalyst, which is a 2:1 layer-lattice aluminosilicate mineral, having a structure that is not capable of acting as a molecular sieve. It discloses the removal of nitrogen from the feed, but limits itself also to the removal of amines from acid gas scrubbing. United States Patent Application 2002/103406 A1 discloses a process for oligomerising an olefin, originating from an oxygenate to olefin process, using a nickel based catalyst. The olefin stream in the process of US 2002/103406 has a low nitrogen content, as low as 0.3 ppm by weight. This stream is therefore very suitable for oligomerisation using nickel based catalysts, because these are known to be particularly sensitive to poisons, such as nitrogen compounds. The process in US 2002/103406 does not comprise a treatment to remove nitrogen from the oligomerisation feed and is not using molecular sieves as oligomerisation catalysts.

United States Patent Application 2004/0097773 A1 discloses a process for oligomerising isobutene. It discloses the removal of nitrogen components from the feed stream, including acetonitrile and N-methyl-pyrrolidone. Both compounds are nitrogen-containing Lewis bases. The catalyst used in US 2004/0097773 is a solid, acidic ion exchange resin in which some of the acidic protons have been exchanged for a metal ion.

United States Patent Applications 2005/0137442 A1 and 2005/0152819 A1 disclose the removal of nitrogen compounds, including a number of Lewis base compounds such as acetonitrile, N-methyl-pyrrolidone, morpholines such as N-formyl morpholine, pyridine and quinoline, from aromatic feedstocks to aromatic conversion processes using molecular sieve catalysts. These publications are not concerned with the feeds to oligomerisation processes using such catalysts, and which operate at different conditions.

We have now found that these weaker nitrogen-containing Lewis bases, when they occur in the feedstock to oligomerisation processes that employ molecular sieve catalysts, can have a surprisingly strong catalyst deactivating effect in spite of their reputation as only weak bases. Thus, there remains a need for an oligomerisation process using a molecular sieve catalyst, which process is capable of handling feedstocks comprising nitrogen-containing Lewis base components.

SUMMARY OF THE INVENTION

The invention provides for a process for the oligomerisation of olefins comprising:
(a) treating an olefin-containing hydrocarbon stream comprising an organic nitrogen-containing Lewis base to thereby lower the concentration of the organic nitrogen-containing Lewis base in the olefin-containing hydrocarbon stream; and (b) subsequently contacting the treated olefin-containing hydrocarbon stream with a molecular sieve oligomerisation catalyst.

DETAILED DESCRIPTION

We have found that the catalyst life for the molecular sieve catalyst is improved when the concentration of the Lewis base is lowered to a level of at most 5 ppm by weight, based on the total hydrocarbon stream, preferably at most 2 ppm, more preferably at most 1 ppm by weight.

The process according to the invention provides the benefit that olefin-containing feedstocks further comprising an organic nitrogen-containing Lewis base may be used for the oligomerisation of olefins over molecular sieve, e.g. zeolite oligomerisation catalysts, after the lowering of the concentration of the Lewis base, and that reactor run lengths and catalyst lives become comparable to oligomerisation processes using feeds not comprising an organic nitrogen-containing Lewis base.

Techniques for treating hydrocarbon streams for lowering the concentration of organic nitrogen-containing Lewis bases may be found for instance in US 2005/0137442 and US 2004/0097773 A1, which are by reference incorporated herein.

Also European Patent 1002852 B1 discloses techniques suitable for nitrile removal from olefin-containing hydrocarbon streams, which are then used as feedstocks for an etherification process for the production of ethers such as MTBE, ETBE or TAME. EP 1002852 B1 is also incorporated herein by reference.

In one embodiment, the treatment step (a) comprises an extraction step, preferably a plurality of extraction steps, which may be in parallel, but preferably are combined in series. A preferred embodiment comprises the use of a multistage countercurrent extraction column. Such a column may comprise from 4 to 10 theoretical stages, preferably 6, 7 or 8. As the stage efficiency may be only 50%, or depending on hydraulics even only 15%, the number of actual stages may be from 8 to 50, preferably from 10 to 35, more preferably from 12 to 25, most preferably from 14 to 18.

A preferred extraction step is a water wash, because of the ready availability of suitable wash water. It is preferred that the pH of the wash water is not too high, such as at most 9.5, but preferably it is at most 9 and more preferably at most 8. Most preferably the water is slightly acidic, with a pH below 6.5, 6, 5 or even 4.

Another advantage of using water in the extraction step is that the waste water that is produced, and which will contain in addition to the extracted Lewis base also dissolved organics, may be suited for reuse in another process step, such as a caustic tower, in a different process, or possibly even in a different step of the process according to the invention, such as an upstream sulphur removal step, for instance in a fluid catalytic cracking treatment of the $C_3/C_4$ fraction or in a steamcracking process that may be providing some or all of the feed to the oligomerisation process.

Preferably, the wash water is not a potential source for introducing an organic nitrogen-containing Lewis base itself, or even a Bronsted base. This could occur when the wash water is treated with a base-containing compound, such as an amine or a morpholine, which could be present in a corrosion inhibitor. It is therefore preferred to use demineralised water as a source of wash water, because of its purity. However, that is not always readily available at the location of the treatment step, and therefore boiler feed water or steam condensate may also be used. These are typically de-aerated and may already comprise a corrosion inhibitor. Even when such a corrosion inhibitor comprises a basic nitrogen compound, we have found that its presence does not necessarily affect the oligomerisation catalyst performance, due to its affinity for the water phase and its typical low concentration.

The performance requirement for treatment step (a) depends on the starting concentration of the organic nitrogen-containing Lewis base before treatment, and the desired concentration thereof at the point of contacting the treated olefin-containing stream with the molecular sieve oligomerisation catalyst. The performance of a countercurrent water wash column is affected by the ratio of water wash flow to hydrocarbon flow, and we have found that a column operating with a ratio of 0.1 to 1.7 on a liquid volume basis is preferred, more preferably a ratio of 0.3 to 1.0. Because of the possibly significant difference in density between water and the hydrocarbon streams, the water to hydrocarbon ratios on a weight basis may be for example from 0.25 to 1.0, preferably from 0.3 to 0.8, more preferably from 0.35 to 0.7 and most preferably from 0.4 to 0.6.

Some of the Lewis bases have a lower affinity for water than others. For instance, propionitrile is less water soluble than acetonitrile. This may make an extraction step less preferred or insufficiently effective in lowering the Lewis base concentration. Therefore in a further embodiment, the treatment step (a) may comprise an adsorbent treatment, using a solid material, catalytic or non catalytic, acting as a sorbent capable of adsorbing said Lewis base. This adsorbent step may be upstream of the extraction step, but is preferably placed in between the extraction step and the oligomerisation reaction. It may also replace the extraction step altogether. An activated alumina (aluminium oxide), such as Selexsorb CD-X, or an acidic ion exchange resin such as DOW M-31 that comprises sulphonic acid may for instance be used in cases when the adsorbent treatment is employed.

In another embodiment, the olefin-containing hydrocarbon stream comprises isobutylene, possibly in concentrations of at least 15% wt, 18% wt, 22% wt, or even higher, e.g. at least 40 or 44% wt. Depending on the desired end-product of the oligomerisation process, it may be desirable to lower the concentration of isobutylene. This may be achieved by the selective conversion of a significant portion of the isobutylene present in the stream to methyl tertiary butyl ether (MTBE) or ethyl tertiary butyl ether (ETBE) by etherification with respectively methanol or ethanol, the dimerisation to di-isobutylene (DIB), or the oligomerisation to another isobutylene oligomer, or the polymerisation to polyisobutylene (PIB), or by the conversion to a higher carbon number hydrocarbon boiling in the range of gasoline, distillate or lubricant oil, followed by a separation of the unreacted material from the product of this conversion. Many of these conversion processes for isobutylene comprise solid materials and/or catalysts that can act as a sorbent capable of adsorbing said Lewis base.

We have found that byproduct streams from etherification processes as discussed above may also be suitable feedstocks for the oligomerisation process of the present invention. In such circumstances, the treatment step (a) for lowering the Lewis base may be located upstream of the etherification process, and hence protect both processes together.

We have found however, that the catalysts used in etherification processes are less affected by organic nitrogen-containing Lewis bases, such as acetonitrile or propionitrile, than are molecular sieve oligomerisation catalysts. Because the etherification processes are less susceptible to these Lewis bases, any upstream treatment step for lowering the concentration thereof may therefore only be operated at moderate severity. Measurable amounts of Lewis bases may then be left in the feed to the etherification process, and the life of its catalyst may still be acceptable. We have found that the unreacted byproduct streams from such etherification processes may still contain measurable amounts of such Lewis bases, meaning that not all of the Lewis bases are adsorbed on the etherification catalyst. The reason for this is believed to be that the acidity of the etherification catalyst is too weak to bond the weak Lewis bases. The concentrations thereof in the byproduct streams may still be significant, and render these byproduct streams less suitable for oligomerisation over molecular sieve catalysts. When there is an etherification reaction performed upstream of the oligomerisation process of the invention, the treatment step to lower the concentration of the Lewis base according to the invention upstream of the etherification reaction may need to be operated at a higher severity as compared to the feed treatment normally employed when only the etherification catalyst needs to be protected.

On the other hand, if no etherification step takes place upstream of the oligomerisation, the treatment step (a) of the process of the invention needs to reach the desired concentrations of said Lewis base by itself, and may then need to be carried out at an even higher severity.

The ExxonMobil Olefins to Gasoline (EMOGAS) process was described at the Annual Meeting of the National Petrochemical and Refiners Association, 13 to 15 Mar. 2005, at the Hilton Hotel, San Francisco, Calif., USA. The presentation given at that meeting is believed to have described olefin oligomerisation employing a zeolite catalyst. The paper relating to that presentation discloses the first commercial scale trial in a tubular reactor on a feed obtained from catalytic cracking (FCC) in which no acetonitrile and propionitrile could be found by nitrogen analysis. The paper also announces a second trial in a chamber reactor, but for which first the feed nitrogen will have to be reduced to acceptable levels by modifying the water treatment wash. The paper does not specify what nitrogen analysis technique was employed (hence what the detectable limits of acetonitrile and propionitrile may have been); nor does it say what levels are acceptable.

It is noted that the treatment steps for lowering the concentrations of these weak Lewis bases in the olefin-containing hydrocarbon streams may involve complex process steps, and may therefore lead to the production of significant amounts of undesired byproducts, such as solid sorbents and/or liquid discard streams, which are difficult to regenerate or dispose of because of their content of organic or other potentially harmful material. It is therefore desirable to also limit the amount of undesired byproducts from the treatment step (a). This may be achieved by not removing the Lewis bases down to unmeasurable concentrations, such as the unmeasurable concentrations measured (but not detailed) in the EMOGAS paper referred to above.

We have now found that organic nitrogen-containing Lewis bases, such as acetonitrile or propionitrile, can be tolerated in olefin-containing hydrocarbon feeds to molecular sieve oligomerisation reactions at concentrations of 0.1 ppm wt or above, preferably 0.2 ppm wt or above, more preferably 0.3 ppm wt or above and most preferably 0.4 ppm by weight or above, based on the total hydrocarbon feed to the molecular sieve oligomerisation catalyst.

The invention therefore also provides for a preferred embodiment of the process wherein the concentration of the organic nitrogen-containing Lewis base in the olefin-containing hydrocarbon stream prior to contacting with the molecular sieve oligomerisation catalyst is not less than 0.1, preferably not less than 0.2, and more preferably not less than 0.3 ppm and most preferably not less than 0.4 ppm by weight, based on the total hydrocarbon feed.

The preferred concentration of said Lewis base in the hydrocarbon feeds being contacted with the molecular sieve oligomerisation catalyst is from 0.1 to 2.0 ppm by weight based on the total hydrocarbon stream, preferably from 0.2 to 1.5 ppm by weight, more preferably from 0.3 to 1.0 ppm by weight, and most preferably from 0.4 to 0.8 ppm by weight.

This embodiment brings the further benefit that the burden of regenerating or discarding the undesired byproducts from the treatment step (a) is reduced.

The olefin-containing feeds that are used for oligomerisation processes are typically obtained from petroleum refining or petrochemical operations. In particular they may be obtained from steam cracking or catalytic cracking, or alternatively from the dehydrogenation, of hydrocarbon streams obtained from the processing of crude oil, natural gas, or field condensates. The compositions of these olefin-containing feeds depend upon the feed to the process that generates the olefins and the conditions that are employed. The capabilities of the petroleum refining and petrochemical operations continue to expand, and are now processing starting materials that contain much higher levels of contaminants. For example, refineries are now processing much more high nitrogen containing crude oils. Steamcrackers are now processing gasoils with higher levels of nitrogen and sulphur. Recently steamcrackers have been developed to process whole crude oils or the heavy fractions from crude oil distillations. Such feedstocks contain particularly high levels of nitrogen or sulphur. Examples of steamcracking process suitable for such feedstocks are described in WO 2005/113718 A2, WO 2004/005433 and WO 2004/005431, which are incorporated by reference. These higher impurity levels in the starting materials may cause the levels of organic nitrogen-containing Lewis base to rise in the derived olefin-containing hydrocarbon streams intended for oligomerisation. Concentrations of at least 1, 2 or 5 ppm weight, based on the total hydrocarbon stream, are more frequently encountered, and they can occasionally be as high as 10, 12 or 30 ppm wt, and less frequently even as high as 30 or 40 ppm by weight.

The olefin-containing feed for the oligomerisation process may be a $C_2$-$C_6$ olefin, and may contain an olefin selected from the group consisting of ethylene, propylene, butene-1, isobutylene, trans-butene-2, cis-butene-2, (normal) pentene-1, (normal) pentene-2,3-methyl-butene-1,3-methyl-butene-2,2-methyl-butene-1,2-methyl-butene-2 and mixtures of any two, three, four or more olefins selected therefrom.

In industrial processes the olefin-containing feeds for the oligomerisation reaction may have been subjected to other treatment before oligomerisation. A typical treatment step is the lowering of the concentration of polyunsaturated compounds, such as one or more diene and/or acetylenic compound, which in particular may be acetylene, methylacetylene, propadiene, 1,3-butadiene, 1,2-butadiene, ethylacetylene, vinylacetylene, or at least one of the members of the family of $C_5$ dienes and acetylenes. The concentration of these polyunsaturated compounds is lowered because they pose a problem for many catalysts at more than trace levels. For molecular sieve oligomerisation catalysts, the concentration of butadiene is desirably at most 7000 ppm, preferably at most 5000 ppm, more preferably at most 2500 ppm, even more preferably at most 1000 ppm, yet more preferably at most 500 or even 100 ppm by weight, based on the total hydrocarbon stream. For acetylene, methylacetylene and propadiene, the concentrations thereof are collectively preferably at most 1000 ppm, more preferably at most 500 ppm, and even more preferably at most 100 ppm, taken all three together.

Typical treatment steps to lower the concentrations of a diene or acetylene include their selective hydrogenation to the corresponding olefin and/or paraffin, the fractionation of acetylene or of a mixture of methylacetylene and propadiene (MAPD), which typically also further comprises some propylene and/or propane, as well as extraction of the diene and/or acetylene.

Some of these treatment steps may also introduce organic nitrogen-containing Lewis base into the hydrocarbon stream that is fed to the oligomerisation process. For example, butadiene concentration may be lowered in steamcracking crude $C_4$ streams, using extraction or extractive distillation employing solvents such as dimethylformamide (DMF), N,N-dimethyl acetamide, β-methoxy propionitrile or N-methyl-pyrrolidone (NMP), or solutions thereof, With an upstream process step that employs such organic nitrogen-containing Lewis base as a process component, the concentrations of said Lewis base in the olefin-containing hydrocarbon stream before treatment step (a) may be as high as 50, 100 or upon excursions even 300 ppm by weight, based on the total hydrocarbon stream.

The term "olefin conversion", as used throughout this application, means the percentage of fresh olefin in the olefin-containing feed to oligomerisation that has reacted (and hence is not retrieved anymore in the stream(s) leaving the process). It may be determined by making a material balance for the feed olefins over the reactor/process and calculating % conversion as 100 times (In−Out)/In.

Throughout an extended production run, the molecular sieve catalyst is subject to deactivation, and the reaction temperature is generally increased over the course of the run to maintain the desired level of olefin conversion. The reaction is generally terminated when a certain temperature, which may represent the limits of the apparatus, is required for achieving the desired level of conversion. In oligomerisation, catalyst life is typically expressed as the amount (weight) of oligomer (sometimes called polymer) made per amount (weight) of catalyst, which provides a value that compensates for throughput variations, and is a result from a material balance over the process throughout the run.

The oligomerisation may be performed in tubular or chamber reactors, though tubular reactors are preferred because of their capability to make better use of the heat of reaction, their ease of startup, in particular for bringing up to reaction temperature, and their tolerance for higher olefin concentrations (also called "olefin strengths") in the stream that is brought in contact with the catalyst. They can also be designed to have a more uniform temperature distribution over the reactor. Chamber reactors are sometimes preferred because of their typically larger catalyst loading and hence longer reactor run length, when a smaller volume of olefin feed is available, for their lower operating pressure, or for their higher operational flexibility.

Tubular reactors employing molecular sieve catalysts typically comprise one or more bundles of tubes also termed "reactor tubes", mounted, preferably vertically, within a shell. The tubes are packed with the catalyst typically in the form of pellets and the feed containing olefin reactant is passed through the tubes in which it is converted, typically from top to bottom. The length of the tube in industrial practice is generally from 2 to 15 meters, often from 3 to 14 meters, preferably from 5 to 12 meters, more preferably from 6 to 11 meters, yet more preferably from 8 to 10 meters. Carbon steel is a typical tube material, but Duplex stainless steel is a preferred material for manufacture of the tubes.

Any convenient number of tubes may be employed in a tubular reactor shell. Typically, operators use from 25 to 500 tubes per shell, arrayed in parallel. Preferred reactors contain about 77 tubes or 180 tubes per shell, although any number may be employed to suit the needs of the operator, e.g. 360 or 420. One reactor may comprise multiple bundles of tubes, for example up to 7 or 8, or even 9 bundles. Hot oil may be used as the temperature control fluid, but more preferably boiling water is used, under pressure to control the temperature.

The present invention may also be applied to oligomerisation reactions performed in adiabatic or chamber type reactors. These typically employ a plurality of adiabatic reaction zones in series, with a means of temperature control between the individual reaction zones. In one embodiment, these reaction zones are separate reactors that each contain at least one catalyst bed, and temperature control may then conveniently be accomplished using heat exchangers between the reactors. As an alternative, a chamber reactor may be employed, where several catalyst beds may be provided within one reactor vessel, and temperature control is provided by interbed quench. A convenient quench fluid in an oligomerisation process may be part of the mixture of unreacted olefins and paraffins that is left over after the oligomerisation reaction, and which may be separated from the oligomer product downstream of the reaction zone.

Historically, oligomerisation reactions over acid catalysts are performed in the presence of water. U.S. Pat. No. 5,672,800 (WO 93/16020) is concerned with the oligomerisation of olefins employing a zeolite catalyst, particularly the zeolite ZSM-22. U.S. Pat. No. 5,672,800 indicates that under the conditions employed in U.S. Pat. No. 5,672,800 conversion and catalyst life can be improved if the oligomerisation is performed in the presence of from 0.05 to 0.25 molar % of water, based on the hydrocarbon content of the feedstock. The compositions in the examples show a significant improvement in catalyst life when water is present.

It has been standard practice to hydrate the feed to oligomerisation reactors in order to prevent excessive temperatures being generated, particularly at the start of a reaction run when the feed contacts fresh catalyst and the exotherm is at its highest. As stated previously, U.S. Pat. No. 5,672,800 relates to the hydration of olefin feeds to oligomerisation, to control temperature and reduce the exotherm. A zeolite catalysed oligomerisation plant is typically equipped with an upstream process step assuring there is enough water in the feed to the reactor to suit the needs of the catalyst. This is typically in the form of, or combined with, a water wash to remove strong basic compounds from the feeds, and the water wash step is therefore preferentially done using a slightly acidic water stream. In one embodiment, the treatment step (a) is combined with this water wash and hydration step.

Also sulphur is undesired in oligomerisation processes. Sulphur removal from such light hydrocarbon streams is typically done by washing with an aqueous solution of an amine, such as mono-ethanol-amine (MEA) or di-ethanol-amine (DEA), or with aqueous caustic soda. This is typically performed upstream of the hydration step, as well as upstream of treatment step (a) of the invention.

The present invention is particularly useful when applied to the oligomerisation process described in copending Patent Application GB 0512377.3.

In the case where the Lewis base is a nitrile, the nitrile content of the feed may conveniently be measured by on line gas chromatography, preferably but not necessarily combined with a mass spectrometry, performed on the feed to the reactor. Polar GC columns are preferred because they separate more readily the polar compounds from the sample matrix. By way of example, a GC-MS having a GC-column FFAP (which stands for Free Fatty Acids Phase, and in this case is a nitroterephthalic acid modified polyethylene glycol phase) with dimensions of 50 m×0.32 mm ID and a coating layer having 0.5 μm dry film thickness, has been used to measure nitrites in C3 and/or C4 streams that resemble liquefied petroleum gas (LPG) streams. One method is to program the oven temperature to stay at 60° C. for 10 minutes and then to raise to 220° C. at a rate of 10° C. per minute. The injector temperature may be 200° C., and the injection volume 1 μl via a liquid sampling valve. Further preferred parameters include a split of 1/10, and Helium as the carrier gas, at a constant rate of 1.0 ml/min. The MS-parameters may be for example: Thermo Voyager MS apparatus, Ionization mode EI+ (Electron Impact Plus), Detector voltage 500 V, GC-interface temperature 210° C., acquisition type: Selected Ion Monitoring (SIM), ion mass/charge (m/z)=41. Quantification may be obtained by injecting a liquefied gas (LPG-type) standard with a known amount of acetonitrile as external standard. A detection limit of 0.2 ppm wt for acetonitrile is readily achievable using this technique.

Other methods proposed in literature include a GC-LOWOX analyzer, using a CP-Lowox column of 10 m by 0.53 mm ID and 10 μm film thickness and a CP-Sil 5 CB Ultimetal column of 25 m by 0.53 mm ID and 0.5 μm film thickness. The LOWOX system comprises a switching device that may send part of the sample from one column to the other. The first column (CP-SIL 5CB) is typically non-polar and serves as a stripper column for heavy hydrocarbons, if any would be present. The second column (CP-LowOx) is typically very polar ad serves as the analytical column. The proposed temperature programme is 5 minutes at 50° C., and ramping to 240° C. at a rate of 20° C./minute. The method further uses helium as the carrier gas, an FID detector, an injection volume of 0.2 μl, and direct injection with a liquid sampling valve (LSV), optionally combined with a backflush, depending on the sample nature such as its average carbon number and carbon number distribution. This method may be applicable for a wider range of samples and a wider selection of Lewis bases. It does not require the use of a mass spectrometer and/or an MS-detector, in particular when references of target components are available and the separation is sufficient.

Another suitable analytical technique is by Nitrogen Chemiluminescence GC. Such method may employ a GE Analytical (formally Sievers) Nitrogen Chemiluminescence Detector (NCD) mounted on an Agilent 5890 GC. Organic samples are typically completely combusted in a dual plasma burner. The NO produced may then be sent to an ozonizer that forms excited $NO_2$. The photochemical decomposition of the excited $NO_2$ may then be detected by a wavelength selective photomultiplier tube. The GC column preferably is an RTX-1 of 30 m by 0.32 mm ID with a 1 μm film. The oven temperature programme is preferably isothermal (holding 5 minutes at 60° C.) for $C_3$ and/or $C_4$ containing (LPG-type) samples. The apparatus may be equipped with a 2 μl high pressure liquid sampling valve. The injector temperature preferably is 200° C., helium may be used as the carrier at a total flow of 25.2 ml/min, a split ratio of 10.0/1, a split flow of 20 ml/min and a column flow of 2 ml/min. The NCD conditions are: hydrogen set at 4.0 ml/min, oxygen at 11.9 ml/min, a pressure of 102 mm Hg, and a temperature of 960° C. Quantification may be performed against a standard blend. The achievable detection limit using this technique is readily 0.2-0.3 ppm wt, and lower amounts, in the range of 0.1-0.15 ppm may be seen under low noise conditions.

We have found that, in processes according to the invention, feeds of single olefins and mixtures of olefins can be processed in tubular reactors employing a zeolite catalyst over extended runs, for example up to 250 days continuous operation, without undesirable loss of catalytic activity. We have found that catalyst life in excess of 1500 tonnes of oligomer per tonne of catalyst may be achieved. The maximum concentration of olefin in the feed that can be processed will depend upon the nature of the olefin or mixture of olefins that are to be oligomerised. However, we have found that propylene containing feeds that contain e.g. up to 65 wt % propylene, more typically up to 60 wt % propylene, most typically up to 55 wt % propylene can be employed. Similarly we have found that butene-containing feeds that contain e.g. up to 80 wt % butene such as up to 70 wt % butene, typically up to 65 wt % butene, most typically up to 60 wt % butene can be processed. Similar amounts can be processed when mixed feeds are employed. The minimum amount of olefin in the feed, according to the invention, is preferably 42 wt %. In the case where the feed contains propylene, the more preferred minimum is 44 wt %, yet more preferably 46 wt % and most preferably 48 wt %. In the case where a butenes feed is employed, the more preferred minimum is 46 wt %, yet more preferably 50 wt %, such as at, least 55 wt % and most preferably at least 60 wt %.

The temperature of a tubular reactor is conveniently controlled in the range of 160 to 300° C. The feed material is fed to the reactor under a pressure such that the material exiting from the outlet of the tubular reactor is maintained at a pressure of at least 55 barg, and thereby the inlet pressure will also be greater than 55 barg. We also prefer to keep the space velocity of the olefin feed relatively high, for example above 1 wt/wt/hour.

We have found that the higher the concentration of saturates and the lower the concentration of olefins in the fresh feed to the oligomerisation process, the lower is the desired concentration of organic nitrogen-containing Lewis base in the fresh feed. This is because the performance measure for the molecular sieve catalyst typically is its life between regenerations, and expressed as a productivity in tons of oligomer produced per ton of catalyst. At a standard conversion, the amount of oligomer produced is directly linked to the amount of olefin that is fed. With the concentration of the Lewis base expressed on the basis of the total hydrocarbon feed stream, there is more Lewis base entering per unit of olefin if the concentration of the olefin is lower. And because the Lewis base poisons the active sites on the molecular sieve catalyst, the catalyst activity will then decay faster on a curve expressing an activity measure related to the catalyst life or productivity expressed as stated.

By fresh feed that is rich in olefin is meant for example, in the case of a propylene feed, a feed containing at least 70 wt %, at least 85 wt %, at least 92 wt % or at least 97 wt % propylene. In the case of a butenes feed, it is meant a feed containing at least 65 wt %, at least 80 wt %, at least 90 wt % or at least 94 wt % butenes. Isobutylene may be present in proportions as low as 1 wt % or 0.5 wt % or less; or alternatively in higher amounts such as up to 18 wt % or up to 22 wt % based on total fresh feed.

The reactor tube may be filled with a more active catalyst in the bottom of the tube (part near the outlet) for a downward flow process, and a less active catalyst in the upper (inlet) part of the tube. Such an arrangement is disclosed in our copending patent application PCT/EP2005/005785.

Multiple reactors may be put in series, with the upstream reactors optionally running with colder steam temperatures than the downstream ones. The reactors in series may also use different catalyst types, and may run at the same or at different temperatures. Similar to recycling of part of the unreacted molecules that are separated from the oligomer product, this allows running high space velocities over a reactor while still reaching high overall conversions. Unlike with solid phosphoric acid (SPA), this is particularly easy to arrange with molecular sieve, e.g. zeolite catalysts, because the pressure drop increase that is typical for SPA catalyst is not observed with these catalysts.

The invention is particularly but not exclusively concerned with processes suitable for the production of $C_5$ to $C_{20}$ olefins boiling in the range of 30° to 310° C., preferably 30° to 300° C., more preferably 30° to 250° C., from propylene and/or butene and/or amylene feedstocks or their mixtures, though ethylene may be present as well. In particular the invention is concerned with the production of the olefins shown in the following table.

The alkenes that may be oligomerised by the processes of the invention include propene, and linear or branched $C_4$-$C_6$-alkenes, which may be mono-, or di-polyunsaturated. The process is particularly advantageous for the oligomerisation of propene and butenes, especially isobutylene, and may be used for the oligomerisation of a single alkene, or of mixtures of alkenes of the same or of different carbon numbers. Oligomers that may be produced by the process of the present invention are

| Oligomer Products | Distillation Range (° C.) ASTM D1078 | |
|---|---|---|
| | Initial Boiling Point | Dry Point |
| Pentenes | 30 | |
| Hexenes | 35 | 72 |
| Heptenes | 88 | 97 |
| Octenes | 114 | 126 |
| Nonenes | 135 | 143 |
| Decenes | 155 | 160 |
| Undecenes | 167 | 178 |
| Propylene Tetramers Or Dodecenes | 175 | 225 |
| Tridecenes | 204 | 213 |

The feed streams containing the feed olefins such as $C_3$ and $C_4$ olefins are generally steams derived from steam cracking or catalytic cracking and the composition of the stream will depend upon the raw material from which it is produced and the production technology employed. However, propylene refinery steams typically contain up to 75 wt % propylene, with the balance being predominantly propane. Similarly, butene refinery steams typically contain up to 70 wt % butenes with the balance being predominantly butanes. Butene streams from steam cracking may contain 90 to 95% butenes, sometimes even 96% wt. The reactivity of the olefins in oligomerisations over zeolite catalysts varies according to the nature of the olefin. With the more reactive olefins, the olefin concentration in the stream fed to the catalyst is typically diluted down to below a certain limit, in order to limit the heat release and keep the heat removal manageable. This problem is less difficult in tubular reactors than in adiabatic-type chamber reactors, thanks to the heat removing fluid they have circulating on the shell side. This issue often has required the expensive addition of diluent to an olefin-containing refinery feed. Typically the diluent may be additional amounts of the alkane found in the refinery feed and/or it may be provided by recycle of the unreacted material derived from the reactor. The need for diluent not only adds to the expense of the operation but it also reduces the volumetric yield of the reaction with associated economic debits.

The molecular sieve catalyst used in the present invention may be any molecular sieve that is active in alkene oligomerisation reactions. For example, there may be used a catalyst selected from the group consisting of zeolites of the TON structure type (for example, H-ZSM-22, H-ISI-1, H-Theta-1, H-Nu-10, KZ-2) or zeolites of the MTT structure type (for example H-ZSM-23, KZ-1) or zeolites of the MFI structure type (for example, H-ZSM-5) or zeolites of the MEL structure type (for example, H-ZSM-11) or zeolites of the MTW structure type (for example, H-ZSM-12), or zeolites of the MWW structure (for example MCM-22, MCM-49 and MCM-56), or zeolites with the EUO structure type (for example, EU-1), or zeolites H-ZSM-57 or H-ZSM-48, or any member of the ferrierite structure family. Other examples of suitable catalysts are offretites, H-ZSM-4, H-ZSM-18 or zeolite Beta. Reference is made to 'Synthesis of High-Silica Aluminosilicate Zeolites' by P. A. Jacobs and J. A. Martens (published as volume 33 in the series 'Studies in Surface Science and Catalysis') for a review of the synthesis and properties of the aforementioned zeolites.

Additionally, the catalyst can be a zeolite synthesised without addition of a template, for example, faujasites, zeolite L, mordenites, erloites and chabazites, the structures of which are contained in the 'Atlas of Zeolite Structure Types' by C. Baerlocher, W. M. Meler and D. H. Olson (published by Elsevier on behalf of the Structure Commission of the International Zeolite Association, $5^{th}$ Revision Edition, 2001). Zeolite catalysts having crystal structures that are essentially the same as the crystal structures of the above-mentioned zeolite catalysts, but differing slightly therefrom in chemical composition, may also be used. Examples include zeolite catalysts obtained by removal of a number of aluminium ions from, or by steaming of, the above-mentioned zeolites catalysts; and zeolite catalysts obtained by the addition of different elements (for example boron, iron and gallium), for example, by impregnation or cation exchange, or by incorporation during the zeolite synthesis.

Another type of molecular sieve suitable for the process of the invention is SAPO-11, which has unidimensional 10-rings like ZSM-22 and ZSM-23.

Mixtures of two or more molecular sieves e.g. a mixture of ZSM-22 and ZSM-57 or ZSM-22 and ZSM-5 can be used as disclosed in EP 0746538 B1. Or alternatively, upon the surface of each zeolite crystal, a layer of another zeolite can be deposited as disclosed in EP 0808298 B1.

The zeolite conveniently has a crystallite size up to 5 μm such as within the range of from 0.05 to 5 μm, for example from 0.05 to 2.0 μm, and typically from 0.1 to 1 μm. An as-synthesized zeolite is advantageously converted to its acid form, for example by acid treatment, e.g. by HCl, or by ammonium ion exchange, and subsequently calcined before use in the process of invention. The calcined materials may be post-treated, such as by steaming. It is also possible to use, as is known in the art, a material in which silicon and aluminium have been replaced in whole or in part by other elements. Silicon may, for example, be replaced by germanium and/or phosphorus; and aluminium more especially by boron, gallium, chromium or iron. Materials containing such replacement lattice elements are also generally termed zeolites, and the term is used in this broader sense in this specification. The zeolites, but also the molecular sieves, might be supported or unsupported, for example in the powder form, or used as an extrudate with an appropriate binder. Where a binder is employed, the binder is conveniently a metal oxide, such as alumina or silica and is present in an amount such that the oligomerisation catalyst contains for example from 1 to 99 wt % of the zeolite or molecular sieve, more preferably from 50 to 70 wt %.

The materials obtained from the process of the present invention will generally be a mixture of desired olefin oligomers, unreacted olefins, diluent (if any is used), water and other impurities. The materials are therefore separated, generally by fractional distillation primarily into the olefin oligomers, the unreacted olefins and, if present, the diluent. The unreacted olefins and diluents may be recycled to the oligomerisation reactor. The olefin oligomers may then be purified as required for use in subsequent reactions. For example the oligomers may contain trace amounts of sulphur which may damage a hydroformylation catalyst. Accordingly, if the olefins are to be used as a feed for hydroformylation, the feed may need to be desulphurised. Similarly the olefin oligomers may contain trace amounts of chlorine which may also be detrimental to hydroformylation catalysts and may need to be removed. If the hydroformylation catalyst is not damaged by sulphur or chlorine, the catalyst in the subsequent hydrogenation step to produce the alcohol derivatives may be damaged by these compounds, and hence sulphur and chlorine are preferably removed, most preferably to very low levels. Furthermore the olefin oligomers themselves are frequently mixtures of oligomers of different carbon number. For example oligomerisation of a mixture of propylene, butene and amylene can result in a mixture of $C_6$ to $C_{13}$ oligomers and this mixture can then be separated by fractional distillation to obtain the oligomer or oligomer mixtures desired for a particular purpose.

The process of this invention can be used in connection with the conversion of a mixture of $C_3$ and $C_4$ olefins by oligomerisation to an oligomer having an atmospheric boiling point that is within the boiling range of gasoline or distillate, and which may be used as a liquid fuel blending stock for blending into motor gasoline or distillate. In such an embodiment, the feed will be comprised of at least about 25% by weight of olefins. A typical olefin-containing feedstock to a polymerisation unit for conversion to oligomers in the gasoline boiling range will comprise a mixture of propane, butane, 2-methylpropane, propene, 1-butene, 2-butene and 2-methylpropene, wherein the olefin concentration is in the range from about 35 to about 60% wt. Ethylene and ethane may also be present, albeit typically in minor amounts. However it will be appreciated that the olefin-containing feedstock can have a variety of other compositions which include but are not limited to, other olefins or olefin mixtures, other diluents and the presence of a minor amount of aromatic compounds. In addition olefin concentrations can be used which are outside this range.

In a further embodiment the present invention is used for the oligomerisation of olefins such as ethylene, propylene, butenes and amylenes to produce $C_6$ to $C_{13}$ olefins which can be used as feeds for hydroformylation reactions for the production of aldehydes and alcohols. The aldehydes may then be oxidised to produce acids or hydrogenated to produce alcohols. The alcohols or the acids may then be used in the production of synthetic esters such as plasticiser esters or synthetic lubricants or in the production of surfactants. The olefins may be hydroformylated using low pressure rhodium catalysed hydroformylation technology or high pressure hydroformylation technology which is typically cobalt catalysed, but rhodium is also used. The present invention is particularly useful in the production of feedstocks which are hydroformylated in the manner described in our copending Patent Application WO 2005/058787. Where the aldehydes produced by this method are hydrogenated, this may readily be accomplished by the method described in our copending Patent Application WO 2005/058782.

The synthetic esters obtained from the oligomers produced according to the current invention may be selected from the group consisting of a polyol ester, an ortho-phthalate di-ester, a terephthalate di-ester, an isophthalate di-ester, an adipate di-ester, a trimellitate tri-ester, a benzoate ester, a cyclohexanoate mono-ester and a cyclohexanoate di-ester. The esters may be obtained by the method described in our copending Patent Applications WO2005/021482 and U.S. Ser. No. 60/685,616.

The present invention is further illustrated by reference to the following example.

EXAMPLE

A refinery butene stream containing 90% normal butenes was oligomerised in a tubular reactor comprising a bundle of tubes, containing ZSM 22 as the catalyst. The oligomerisation temperature during the run was between 200 and 300° C., increasing as the run progressed. The reactor inlet pressure was 80 barg and the per pass conversion of butenes was 50 wt %.

Two runs were performed. In the first run, the olefin-containing refinery stream was passed directly to the oligomerisation tubes, and oligomerisation was continued until the temperature had been increased to 300° C. to maintain the target conversion. In the second run, the refinery stream was subjected to a treatment step to lower the level of organic nitrogen-containing Lewis base prior to oligomerisation by means of a continuous countercurrent water wash treatment having 7 theoretical stages, and the treated feed was passed to the oligomerisation reactor.

The olefin-containing feed delivered to the oligomerisation catalyst in the first run contained 3-5 ppm wt of acetonitrile The feed delivered to the oligomerisation catalyst in the second run contained between 0.2 and 0.8 ppm wt acetonitrile, with an average of 0.4 ppm wt. All these concentrations are based on the total hydrocarbon stream.

The catalyst life in tonnes of oligomer produced per tonne of catalyst until the reactor temperature reached 300° C.

| Run | Acetonitrile (wt ppm) | Catalyst life tonne oligomer/tonne catalyst |
|---|---|---|
| (i) | 3-5 | 1000 |
| (ii) | 0.2-0.8 | 2500 |

This demonstrates that under otherwise equivalent conditions, the process of the invention leads to much improved catalyst life by virtue of the treatment step (a).

Furthermore, certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

We claim:

1. A process for the oligomerisation of olefins comprising:
   (a) treating an olefin-containing hydrocarbon stream comprising an organic nitrogen-containing Lewis base to thereby lower the concentration of the organic nitrogen-containing Lewis base in the olefin-containing hydrocarbon stream; and
   (b) subsequently contacting the treated olefin-containing hydrocarbon stream with a molecular sieve oligomerisation catalyst;
   wherein said Lewis base is selected from the group consisting of acetonitrile, propionitrile, dimethylformamide, N-methyl-pyrrolidone, and mixtures thereof;
   wherein the concentration of said Lewis base is lowered to a concentration that is not less than 0.1 ppm by weight and is at most 5 ppm by weight based on the total treated hydrocarbon stream.

2. The process according to claim 1 wherein the concentration of said Lewis base prior to said treatment step is at least 1 ppm by weight, based on the total hydrocarbon stream, and at most 40 ppm by weight on the same basis.

3. The process according to claim 1 wherein the concentration of said Lewis base in the hydrocarbon stream being contacted with said oligomerisation catalyst is from 0.2 to 0.8 ppm by weight, based on the total hydrocarbon stream.

4. The process according to claim 1 wherein the olefin-containing hydrocarbon stream is obtained by catalytic cracking, steamcracking, or dehydrogenation of a hydrocarbon starting material.

5. The process according to claim 1 wherein the olefin-containing hydrocarbon stream further comprises a diene and/or acetylene, and the concentration of diene and/or acetylene is lowered prior to oligomerisation.

6. The process according to claim 5 wherein the diene is butadiene and the butadiene concentration is lowered by an extraction step.

7. The process according to claim 6 wherein the extraction step utilises a compound selected from the group of dimethylformamide, N,N-dimethyl acetamide, β-methoxy propionitrile and N-methyl-pyrrolidone, and is performed prior to said Lewis base lowering treatment step.

8. The process according to claim 5 wherein the concentration of said diene and/or acetylene is lowered by a hydrogenation step.

9. The process according to claim 5 wherein the concentration of said diene and/or acetylene is lowered by a fractionation step.

10. The process according to claim 1 wherein the olefin-containing hydrocarbon stream comprises isobutylene, said process further comprising lowering the concentration of isobutylene prior to oligomerisation.

11. The process according to claim 10 wherein the concentration of isobutylene is lowered by a process selected from conversion to MTBE, conversion to ETBE, conversion to an oligomer of isobutylene, conversion to polyisobutylene (PIB), and conversion to a higher carbon number hydrocarbon boiling in the boiling range of gasoline, distillate or lubricant oil.

12. The process according to claim 1 wherein the treatment step to lower the concentration of said Lewis base comprises an extraction step.

13. The process according to claim 1 wherein the treatment step to lower the concentration of said Lewis base comprises the use of a solid material, catalytic or non catalytic, acting as a sorbent capable of adsorbing said Lewis base.

14. The process according to claim 1 wherein the oligomerisation produces an oligomer having an atmospheric boiling point that is within the boiling range of gasoline or distillate.

15. The process according to claim 14 further comprising blending the oligomer into motor gasoline or distillate.

16. The process according to claim 14 further comprising hydroformylating the oligomer to produce a hydroformylation product comprising an aldehyde.

17. The process according to claim 16 further comprising hydrogenating the aldehyde to produce an alcohol.

18. The process according to claim 17 further comprising esterifying the alcohol to produce an ester.

19. The process according to claim 18 wherein the ester is selected from the group consisting of an ortho-phthalate di-ester, a terephthalate di-ester, an isophthalate di-ester, an adipate di-ester, a trimellitate tri-ester, a benzoate ester, a cyclohexanoate mono-ester and a cyclohexanoate di-ester.

20. A process for making a product selected from the group consisting of MTBE, ETBE, an oligomer of isobutylene, polyisobutylene (PIB), and a hydrocarbon boiling in the range of gasoline, distillate, or lubricant oil, said process including the process according to claim 11.

21. A product made by a process according to claim 20.

22. A product made by the process of claim 17.

23. The process of claim 1 wherein the olefin-containing hydrocarbon stream is a $C_2$-$C_6$ olefin-containing hydrocarbon stream.

24. The process of claim 1 wherein the water washing comprises a water wash that is acidic.

25. The process of claim 1 wherein the water washing comprises a water wash that has a pH of below 6.5.

26. The process of claim 1 wherein the water washing comprises a water wash that has a pH of below 6.

27. The process of claim 1 wherein the water washing comprises a water wash that has a pH of below 5.

28. The process of claim 1 wherein the water washing comprises a water wash that has a pH of below 4.

29. The process of claim 1 wherein the extraction step comprises a multistage extraction.

30. The process of claim 29 wherein the multistage extraction comprises a multistage countercurrent extraction.

* * * * *